United States Patent [19]

Ueda

[11] Patent Number: 5,756,905

[45] Date of Patent: May 26, 1998

[54] AUTOMATIC INJECTOR

[75] Inventor: Masahito Ueda, Kyoto, Japan

[73] Assignee: Shimadzu Corporation, Kyoto, Japan

[21] Appl. No.: 826,402

[22] Filed: Mar. 24, 1997

[30] Foreign Application Priority Data

Apr. 30, 1996 [JP] Japan ................................ 8-134435

[51] Int. Cl.$^6$ .......................................... G01N 1/14
[52] U.S. Cl. .................................................. 73/864.24
[58] Field of Search ......................... 73/61.55, 61.56, 73/61.59, 864.21–864.25, 864.86, 864.87; 422/100

[56] References Cited

U.S. PATENT DOCUMENTS

| | | | |
|---|---|---|---|
| 3,991,627 | 11/1976 | Laird et al. | 73/864.23 |
| 4,499,053 | 2/1985 | Jones | 73/864.25 |
| 4,621,534 | 11/1986 | Munari et al. | 73/864.86 |
| 4,713,974 | 12/1987 | Stone | 73/864.23 |
| 4,951,512 | 8/1990 | Mazza et al. | 73/864.23 |

*Primary Examiner*—R. Raevis
*Attorney, Agent, or Firm*—Kanesaka & Takeuchi

[57] ABSTRACT

An automatic injector is used for introducing a specimen into a specimen analyzing device, such as a gas chromatograph or a liquid chromatograph. The automatic injector is formed of a syringe having a needle at one end and a plunger slidably operationally situated inside the syringe for sucking and injecting the specimen through the needle, a syringe supporting member fixed to the syringe for supporting the same and having a sliding guide, and a needle guide. The needle guide includes a vertical plate portion having a groove for slidably engaging the sliding guide, and a horizontal plate portion fixed to the vertical plate portion and having a needle protection with a hole. A tip of the needle is positioned in the hole to prevent the needle from being bent when the needle is moved downwardly. The automatic injector is driven with a small torque.

7 Claims, 4 Drawing Sheets

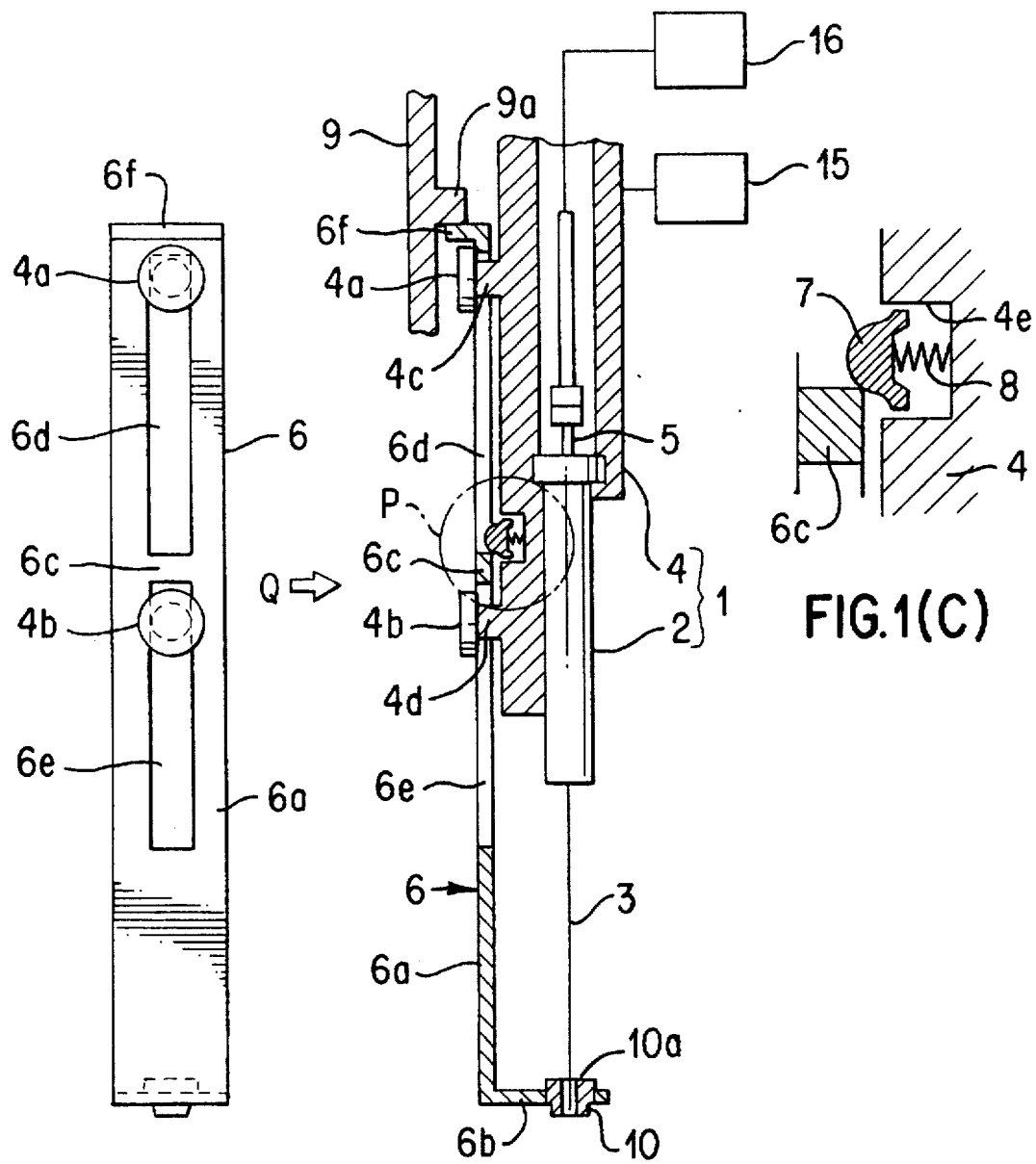

AUTOMATIC INJECTOR

BACKGROUND OF THE INVENTION AND RELATED ART STATEMENT

The present invention relates to an automatic injector or so called autoinjector for introducing a specimen into a device for analyzing the specimen, such as a gas chromatograph or a liquid chromatograph.

In case a specimen is injected or supplied into a device for analyzing the specimen, such as a gas chromatograph, an automatic injector or autoinjector is used. More specifically, as shown in FIG. 4, vials 12 containing specimens are placed in a rack 14, and the rack 14 is moved under a syringe 2; the syringe 2 is moved downward by a syringe driving portion 11 so that a needle 3 is pierced into the vial 12, and the specimen is sucked into the syringe 2; the syringe 2 is elevated, and the rack 14 is moved from this position; and the syringe 2 is lowered to a specimen injection port 13 by the syringe driving portion 11 so that the needle 3 is pierced into the specimen injection port 13, and the specimen in the syringe 2 is injected thereinto. In this case, a needle guide, not shown, for guiding the needle 3 to the specimen injection port 13 is often used in the autoinjector.

In the autoinjector, there are cases where the syringe driving portion 11 is fixed, and the syringe driving portion 11 itself is moved. In the autoinjector where the syringe driving portion is fixed, if the needle guide and the syringe driving portion are not integrally formed, the needle may be bent when it is used since a large force is applied to the needle. In case the needle guide and the syringe driving portion are formed integrally, normally, the needle guide is actuated by a strong spring, so that the needle hardly bends. However, since the needle is driven against the urging force of the strong spring, it is required to use a driving portion, such as a motor, having a large torque. Also, in case the syringe driving portion is moved in the left and right directions, i.e. a horizontal rotating direction, and the needle is pierced into the vial or specimen injection port, it is not necessary to use the strong spring as described above. However, a position alignment device for aligning the needle with the vial or the specimen injection port is required, which raises a cost.

The present invention has been made with reference to the above problems, and an object of the invention is to provide an autoinjector, wherein a needle is not bent when it is pierced into a vial or specimen injection port.

Another object of the invention is to provide an autoinjector as stated above, which can be manufactured at a low cost.

A further object of the invention is to provide an autoinjector as stated above, which can be driven with a small torque.

Further objects and advantages of the invention will be apparent from the following description of the invention.

SUMMARY OF THE INVENTION

An automatic injector or autoinjector of the invention is designed to suck and inject a specimen, i.e. sucking a specimen from a vial and injecting into a specimen injection port.

The autoinjector is basically formed of a syringe having a needle at one end and a plunger slidably operationally situated inside the syringe for sucking and injecting the specimen through the needle, a syringe supporting member fixed to the syringe for supporting the same and having a sliding guide, and a needle guide. The needle guide includes a vertical plate portion having a groove for slidably engaging the sliding guide, and a horizontal plate portion fixed to the vertical plate portion and having a needle protection with a hole. A tip of the needle is positioned in the hole to prevent the needle from being bent when the needle is moved downwardly, i.e. pierced into the vial or specimen injection port. When the vertical plate portion is located at an upper position, an upper edge of the vertical plate portion abuts against a fixed portion of a frame of the autoinjector.

The syringe supporting member further includes means for restricting movement of the needle guide relative to the syringe supporting member. The restricting means keeps the needle to be located in the hole of the needle protection.

The restricting means includes a projection with a spring attached to the syringe supporting member, and an engaging member formed in the needle guide. The engaging member may be a cross bar for separating the groove into upper and lower grooves. The projection crosses under the cross bar when the projection is urged against the cross bar.

In the invention, when the needle is pierced into the vial or specimen injection port, the needle protection is located outside the needle. Thus, bending of the needle is surely prevented.

BRIEF DESCRIPTION OF THE DRAWINGS

FIG. 1(A) is a vertical section view of an autoinjector according to the invention;

FIG. 1(B) is a side view from an arrow Q direction in FIG. 1(A);

FIG. 1(C) is an enlarged view of a portion P in FIG. 1(A);

DETAILED DESCRIPTION OF A PREFERRED EMBODIMENT

Figure 2A:
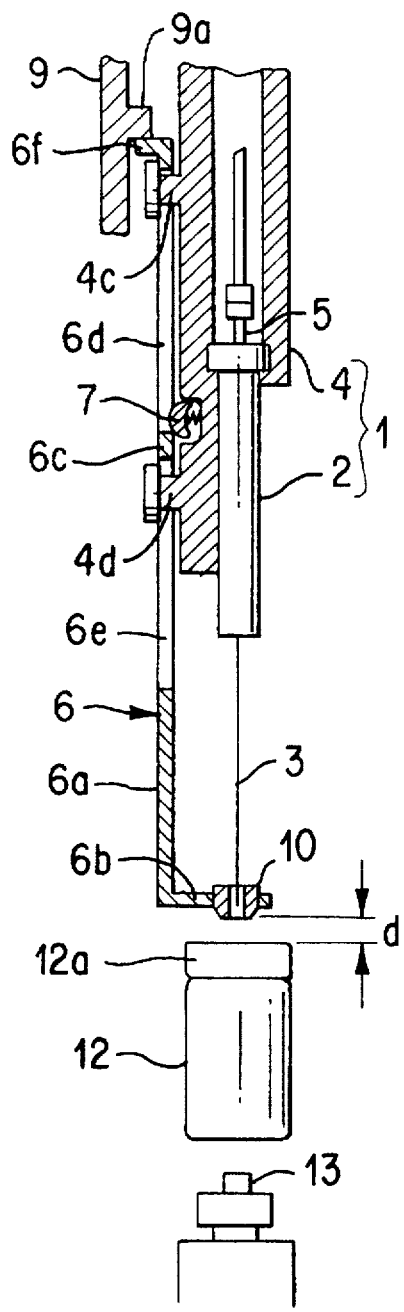
FIG. 2(A) is a vertical section view of a syringe driving portion of the autoinjector according to the invention before a specimen is sucked from a vial.

Hereinunder, an embodiment of the present invention is explained with reference to the accompanied drawings.

FIG. 1(A) is a vertical section view of an automatic injector or autoinjector according to the present invention; FIG. 1(B) is a side view from an arrow Q direction in FIG. 1(A); and FIG. 1(C) is an enlarged view of a portion P in FIG. 1(A). The autoinjector is formed of a syringe driving portion 1 including a syringe 2 provided with a needle 3 for sucking and discharging a specimen and a syringe supporting member 4 for fixing and supporting the syringe 2; and a needle guide 6 attached to the syringe supporting member 4 of the syringe driving portion 1 to slide for a predetermined distance with respect to the syringe supporting member 4.

In the syringe 2, a specimen is sucked and discharged by a plunger 5. In the syringe driving portion 1, the syringe supporting member 4 is connected to a movable portion of a driving mechanism 15, such as pulleys and a timing belt which vertically moves, or pinions and a rack. Also, the plunger 5 is independently driven by a driving mechanism 16, such as a belt and pulleys or pinions and a rack.

The needle guide 6 is formed of a vertical plate 6a and a horizontal plate 6b in an L shape. The vertical plate 6a is provided with two grooves 6d and 6e divided by a cross linking portion (column portion) 6c provided at a middle portion thereof. Also, the syringe supporting member 4 of the syringe driving portion 1 includes sliding guides 4c, 4d provided with extraction preventing portions 4a, 4b. The sliding guides 4c, 4d are inserted into the respective grooves 6d, 6e provided in the vertical plate 6a of the needle guide 6.

A depression 4e is provided at a lower portion of the syringe supporting member 4, and a projection 7 mounted on a spring 8 which does not exert an urging force in a normal position is inserted therein.

When the projection 7 is pushed with a slightly large force by the cross linking or column portion 6c of the needle guide 6, the spring 8 is compressed to thereby allow the projection 7 to cross under the cross linking portion 6c. Namely, in case the projection 7 is located in the upper groove 6d, when the projection 7 is pushed, the projection 7 enters into the lower groove 6e. On the contrary, the projection 7 in the lower groove 6e may enter into the upper groove 6d.

More specifically, when the syringe supporting member 4 is moved downward at a slow speed, the projection 7 engages the cross linking portion 6c of the needle guide 6 and is moved downward together with the needle guide 6. Even if the syringe supporting member 4 is moved downward at a fast speed, the needle guide 6 can be moved downward together with the syringe supporting portion 4 due to the operation of the projection 7.

In the state where the needle guide 6 is moved together with the syringe supporting portion 4, when an operation, such as pushing a septum, is made, the needle guide 6 is blocked by the vial or the like, so that only the syringe 4 is relatively lowered to allow the needle to pierce the vial. Namely, the projection 7 crosses under the cross linking portion 6c and enters into the lower groove 6e of the needle guide 6, so that the syringe supporting member 4 is independently moved downward. Incidentally, the projection 7 is not necessarily required. Therefore, the cross linking portion 6c provided at the middle portion of the vertical plate 6a is not necessarily required, either.

The syringe supporting member 4 for constituting the syringe driving portion 1 and the needle guide 6 are structured as described above, and integrally moved for a predetermined distance. Incidentally, an upper edge 6f of the needle guide 6 is designed to abut against a projecting portion 9a of a fixed portion, such as a frame of an autosampler 9. Therefore, when the syringe driving portion 1, i.e. syringe supporting member 4, is moved upward, in case the needle guide 6 abuts against the projecting portion 9a, the needle guide 6 does not move upward anymore. Incidentally, the horizontal plate 6b of the needle guide 6 is provided with a needle protection 10 having a hole 10a, and a tip of the needle 3 is always positioned in a vicinity of a center of the hole 10a.

The autoinjector of the invention is formed as described above, and the operations about suction and injection of a specimen by the autoinjector are now explained with reference to FIGS. 2 and 3.

First, the suction of the specimen is explained.

Figure 4:
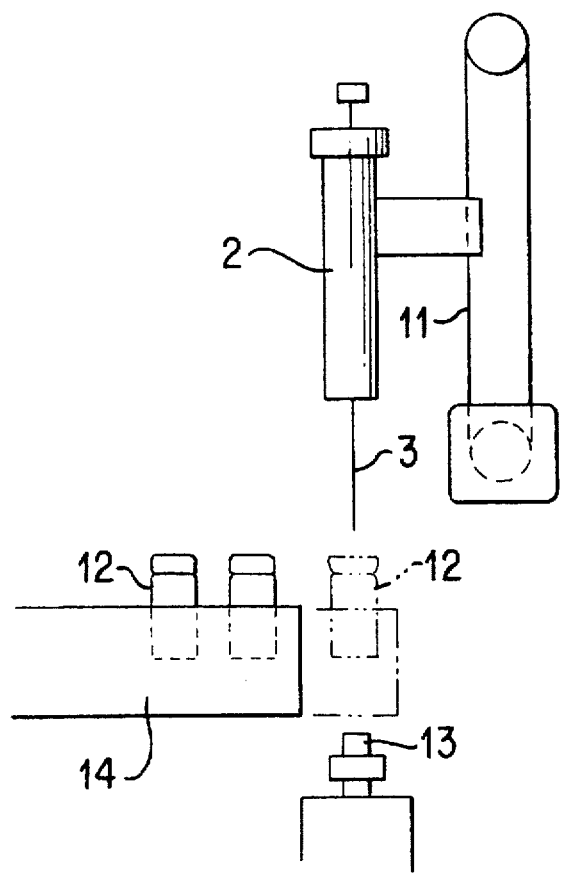
FIG. 4 is a diagram of a conventional autoinjector.

(1) As shown in FIG. 2(A), the vial 12 containing a specimen is moved right under the syringe driving portion 1 from a side direction (refer to FIG. 4).

Figure 2B:
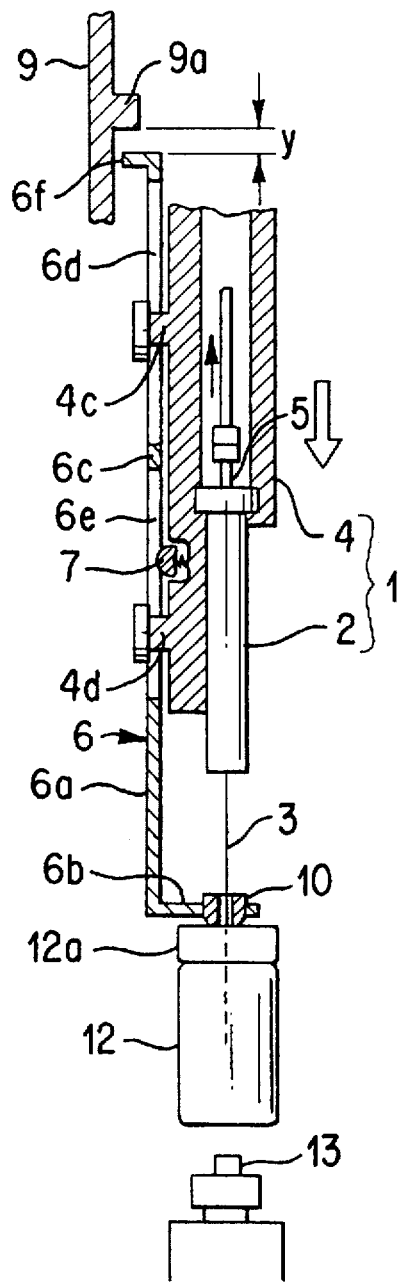
FIG. 2(B) is a vertical section view in a state where the syringe driving portion is moved downward and a needle is pierced into the vial.

(2) Then, as shown in FIG. 2(B), the syringe supporting member 4 of the syringe driving portion 1 is moved downward by the driving mechanism, so that a lower surface of the needle protection 10 provided to the horizontal plate 6b of the needle guide 6 abuts against an upper surface of a cap 12a of the vial 12. At this time, a moving amount $y$ in a lower direction of the syringe supporting member 4 is the same as a distance $d$ between an upper surface of the cap 12a of the vial 12 and the lower surface of the needle protection 10 provided at the horizontal plate 6b of the needle guide 6.

(3) When the syringe supporting member 4 is driven further, the needle guide 6 is stopped here by the vial 12. However, the projection 7 provided in the depression 4e crosses under the cross linking portion 6c of the needle guide 6 and enters into the lower groove 6e, so that the syringe supporting member 4 further moves downward. Then, the needle 3 is pierced into the cap 12a of the vial 12 and reaches the specimen therein. A necessary quantity of the specimen is sucked through the syringe 2 by driving the plunger 5.

Next, the discharge or injection of the specimen is explained.

Figure 3A:
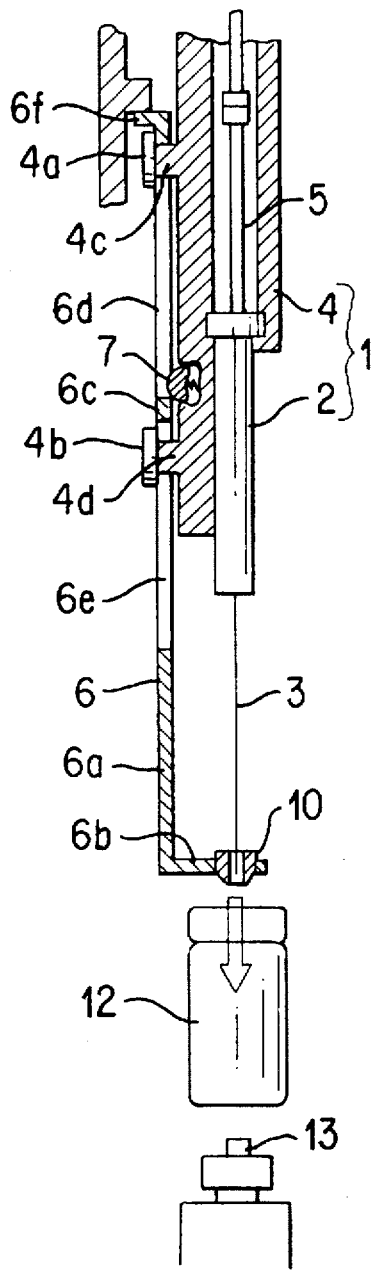
FIG. 3(A) is a vertical section view in a state where the syringe driving portion of the autoinjector of the invention is elevated after the specimen is sucked.

(1) As shown in FIG. 2(B), after a predetermined quantity of the specimen is sucked by the syringe 2, the whole syringe driving portion 1 is moved upward as shown in FIG. 3(A). At this time, since the upper edge 6f of the needle guide 6 abuts against the projecting portion 9a of the fixed portion 9 of the frame, the needle guide 6 is stopped at this point. However, the syringe supporting member 4 is further moved upward, and the projection 7 crosses under the cross linking portion 6c of the needle guide 6 and again enters into the upper groove 6d.

Incidentally, when the syringe supporting member 4 is moved upward, the vial 12 sticking to the needle 3 moves upward together halfway of the upward movement. However, when the syringe supporting member 4 and the needle 3 are elevated, in case the needle guide 6 is stopped, the vial 12 hits the needle protection 10 provided on the horizontal plate 6b of the needle guide 6. Since the needle 3 and the syringe supporting member 4 further move upwardly, the vial 12 automatically drops off onto the rack 14 (refer to FIG. 4).

Figure 3B:
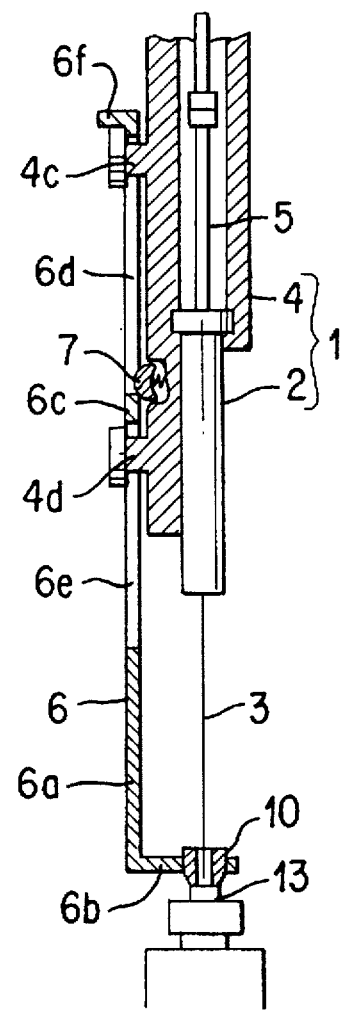
FIG. 3(B) is a vertical section view in a state where the syringe driving portion is moved to a specimen injection port.

(2) After the syringe 2 sucks the specimen, the vial 12 is moved in the transverse direction, and the syringe driving portion 1 is lowered to a specimen injection port 13 which is located right under the syringe 2, as shown in FIG. 3(B). At this time, since the projection 7 engages the cross linking portion 6c of the needle guide 6, the needle guide 6 is also moved together with the syringe supporting member 4. However, when the syringe supporting member 4 is further moved, the lower edge of the needle protection 10 provided on the horizontal plate 6b of the needle guide 6 abuts against the specimen injection port 13 and the needle guide 6 stops.

Figure 3C:
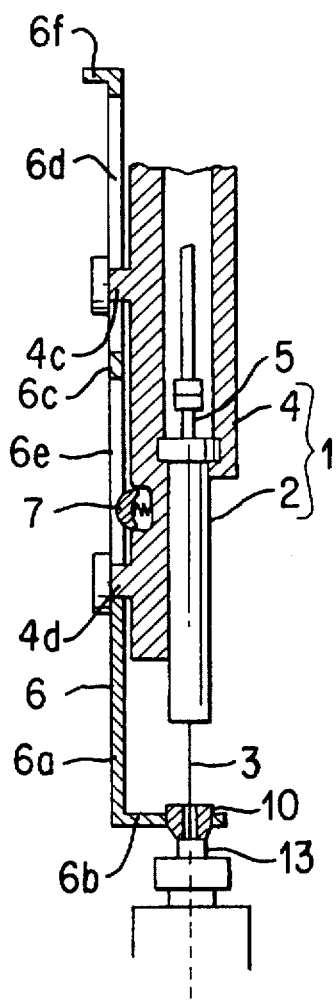
FIG. 3(C) is a vertical section view in a state where the syringe driving portion is moved to the specimen injection port, and the needle is pierced to inject the specimen thereinto.

(3) However, as shown in FIG. 3(C), when the syringe supporting member 4 is further moved downward, the projection 7 provided in the depression 4e of the syringe supporting member 4 crosses under the cross linking portion 6c of the needle guide 6 and enters into the lower groove 6e. Thus, only the syringe supporting member 4 is moved downward, and the needle 3 is pierced into the specimen injection port 13 to enter therein. Then, the specimen in the syringe 2 is injected or ejected by driving the plunger 5.

(4) After the specimen is injected, the whole syringe driving portion 1 is moved upward. However, since the upper edge 6f of the needle guide 6 abuts against the projecting portion 9a of the fixed portion 9, such as a frame, the needle guide 6 stops at this point. However, since the projection 7 crosses under the cross linking portion 6c of the needle guide 6 and enters the upper groove 6d, the syringe supporting member 4 is further moved upward to assume a state as shown in FIG. 2(A).

Incidentally, in the present embodiment of the invention, by changing the positions of the grooves 6d, 6e and the cross linking portion 6c, needles having various lengths can be used.

As described hereinabove, according to the autoinjector or automatic injector of the present invention, when a specimen is sucked from a vial or the specimen is injected, there is no possibility of bending of a needle. Also, a cost for manufacturing the autoinjector of the invention can be reduced. Further, since it is not required to use a strong spring, small driving torque is sufficient.

While the invention has been explained with reference to the specific embodiment of the invention, the explanation is illustrative, and the invention is limited only by the appended claims.

What is claimed is:

1. An automatic injector for sucking and injecting a specimen, comprising, a syringe having a needle at one end and a plunger slidably operationally situated inside the syringe for sucking and injecting the specimen through the needle;

a syringe supporting member fixed to the syringe for supporting the same and having a sliding guide, said syringe supporting member being moved for a predetermined distance; and a needle guide including a vertical plate portion having a groove for slidably engaging the sliding guide, and a horizontal plate portion fixed to the vertical plate portion and having a needle protection with a hole, into which a tip of the needle is positioned to prevent the needle from being bent when the needle is moved, an upper edge of said vertical plate portion being adapted to abut against a fixed portion when the vertical plate portion is located at an upper position.

2. An automatic injector according to claim 1, wherein said syringe supporting member further includes means for restricting movement of the needle guide relative to the syringe supporting member, said restricting means keeping the needle to be located in the hole of the needle protection.

3. An automatic injector according to claim 2, wherein said restricting means includes a projection with a spring attached to the syringe supporting member, and an engaging member formed in the needle guide.

4. An automatic injector according to claim 3, wherein said engaging member is a cross bar for separating the groove into upper and lower grooves, said projection crossing under the cross bar when the projection is urged against the cross bar.

5. An automatic injector according to claim 4, wherein said sliding guide includes upper and lower guides engaging the upper and lower grooves, respectively.

6. An automatic injector according to claim 5, wherein a distance between a lower end of the projection and an upper end of the upper guide is substantially same as a length of the upper groove so that when the vertical plate portion abuts against the fixed portion, the projection is moved from the lower groove to the upper groove, said projection in the upper groove, when the vertical plate portion abuts against a vial, being moved to the lower groove crossing under the cross bar.

7. An automatic injector according to claim 2, further comprising first and second operating means attached to the syringe support guide and the plunger for independently actuating the same.

* * * * *